(12) United States Patent
Ramos

(10) Patent No.: US 8,747,306 B1
(45) Date of Patent: Jun. 10, 2014

(54) ENDOTRACHEAL INTUBATION ASSISTANCE DEVICE AND METHOD OF USE

(76) Inventor: Patricia Ramos, Ware, MA (US)

( * ) Notice: Subject to any disclaimer, the term of this patent is extended or adjusted under 35 U.S.C. 154(b) by 104 days.

(21) Appl. No.: 13/557,569

(22) Filed: Jul. 25, 2012

Related U.S. Application Data

(60) Provisional application No. 61/512,498, filed on Jul. 28, 2011.

(51) Int. Cl.
*A61B 1/267* (2006.01)

(52) U.S. Cl.
USPC .......................................... 600/194; 600/197

(58) Field of Classification Search
USPC ......... 600/114, 119, 120–125, 185–199, 237, 600/239, 240, 241; 128/897, 898, 200.26
See application file for complete search history.

(56) References Cited

U.S. PATENT DOCUMENTS

| | | | | |
|---|---|---|---|---|
| 2,781,760 A | * | 2/1957 | Baer Austin R | 606/167 |
| 5,701,918 A | * | 12/1997 | Jiraki | 128/897 |
| 8,328,843 B2 | * | 12/2012 | Oren et al. | 606/205 |
| 2003/0220542 A1 | * | 11/2003 | Belson et al. | 600/109 |
| 2004/0199204 A1 | * | 10/2004 | Voegele et al. | 606/205 |
| 2011/0120459 A1 | | 5/2011 | Ramos | |

* cited by examiner

*Primary Examiner* — Pedro Philogene
*Assistant Examiner* — Lynnsy Schneider

(57) ABSTRACT

An endotracheal intubation assistance device for use in assisting a practitioner in performing an endotracheal intubation on a patient. The endotracheal intubation assistance device comprises a thumb member which is engaged with a practitioner's thumb thereby creating a protective barrier between the practitioner's thumb and the patient's teeth. The endotracheal intubation assistance device further comprises a blade member which extends beyond a distal side of the thumb member and serves to expose the patient's glottis in an efficient and effective manner, thereby enhancing the accuracy of a digitally performed endotracheal intubation.

11 Claims, 7 Drawing Sheets

ENDOTRACHEAL INTUBATION ASSISTANCE DEVICE AND METHOD OF USE

CROSS REFERENCE TO RELATED APPLICATIONS

This application claims the benefit of U.S. Provisional Application No. 61/512,498 filed on Jul. 28, 2011.

BACKGROUND OF THE INVENTION

1. Field of the Invention

The invention relates to an endotracheal intubation assistance device used to assist in endotracheal intubation. More particularly, the invention relates to an endotracheal intubation assistance device that, when properly applied to a practitioner's hand, assists the practitioner in performing an endotracheal intubation.

2. Background of the Invention

Endotracheal intubation is the process of passing an endotracheal tube through the glottis and into the trachea, just above the corina, to open the airway for purposes of administering oxygen, medication, anesthesia, and the like. Practitioners generally use a laryngoscope to assist them in performing an endotracheal intubation, wherein the laryngoscope is inserted through the mouth and used to aid the practitioner in locating the trachea. A disadvantage of using a laryngoscope is that a patient oftentimes bites down on the laryngoscope thereby causing the patient to crack and/or chip a tooth. Additionally, oftentimes a laryngoscope is not available and/or its use is not desirable. In these cases, a practitioner may opt for performing the endotracheal intubation via digital or tactile means.

When performing a digital, tactile endotracheal intubation on a patient the practitioner does so in a "blind" fashion. That is, while the patient is in a generally supine position, a healthcare practitioner, while face to face with the patient, places four fingers of the practitioner's first hand down into the patient's throat, and with the practitioner's index and middle fingers of the first hand, the practitioner reaches and feels for the patient's epiglottis. Once the epiglottis is located, the practitioner holds his first hand in place forming a passage to the epiglottis. Then, with the practitioner's second hand, which is holding the tracheal tube, passes the tracheal tube through the passage formed by the fingers of the first hand, and attempts to position the tracheal tube into the patient's trachea.

Unfortunately, because the practitioner's first hand is blocking visualization of the patient's trachea, the intubation is performed essentially blindly, and, oftentimes, the tracheal tube passes into the esophagus rather than the trachea. Such a failed attempt at inserting the tracheal tube into the patient's trachea wastes valuable time and patient oxygenation. Another problem inherent in digital endotracheal intubation is that the patient oftentimes bites down on the practitioner's hand while the practitioner is performing the intubation.

Therefore, what is needed is a device capable of efficiently and safely assisting in the performance of a digital endotracheal intubation by providing a device which will allow a practitioner to perform a digital endotracheal intubation with the added advantage of being able to visualize the patient's airway and vocal cords, as well as, to see the passage of the endotracheal tube into the trachea, while simultaneously protecting the practitioner's hand during the endotracheal intubation.

BRIEF SUMMARY OF THE INVENTION

The above-discussed problems are greatly reduced or alleviated by an endotracheal intubation assistance device specially configured to assist a practitioner in viewing a patient's glottis when, e.g., the practitioner is about to perform an endotracheal intubation on the patient, and, more especially, a digital endotracheal intubation. In an exemplary embodiment, the endotracheal intubation assistance device comprises a sleeve having a distal end oppositely situated from a proximal end, wherein the proximal end forms an opening for receiving a thumb of the practitioner, and further wherein, when the sleeve is positioned on the practitioner's thumb, the sleeve extends along at least a portion of the practitioner's thumb which comprises a distal phlange, a proximal phlange, and a metacarpal bone I. The endotracheal intubation assistance device further comprises a blade member which extends from the distal end of the sleeve. The blade member is specially configured to move the patient's tongue in a manner that will allow the practitioner to readily detect the patient's glottis.

BRIEF DESCRIPTION OF THE DRAWINGS

The benefits and advantages of the present invention will become more readily apparent to those of ordinary skill in the relevant art after reviewing the following detailed description and accompanying drawings, wherein.

DETAILED DESCRIPTION OF THE INVENTION

Figure 1:
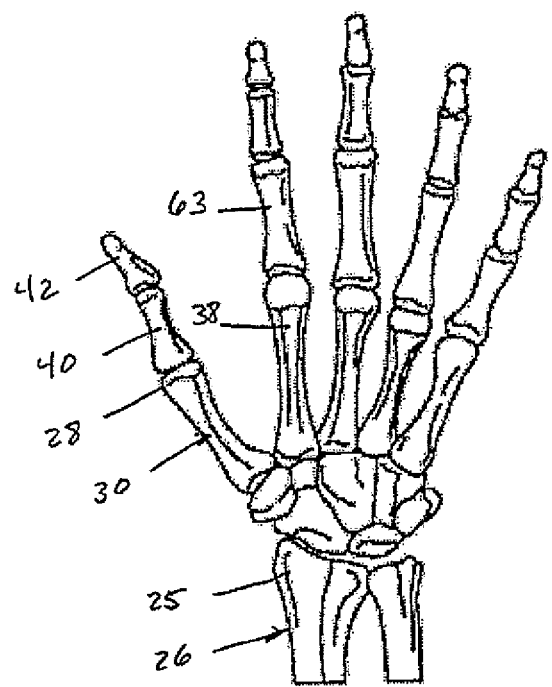
FIG. 1 is a schematic depicting the skeletal bones of a human forearm, wrist, and hand.

Disclosed herein is an endotracheal intubation assistance device configured to remove a patient's tongue from a line of sight, and to further enhance the visibility of the patient's glottis, thereby assisting a practitioner in detecting the location of the patient's trachea for purposes of performing an endotracheal intubation, and, more especially, a digital endotracheal intubation. It is to be understood herein and throughout that the term "patient" shall refer to any animal upon which endotracheal intubations are performed, either presently or in the future, and shall include, for example and without limitation, humans, dogs, cats, horses, and the like.

The endotracheal intubation assistance device comprises a sleeve which is configured to fit onto at least a portion of a practitioner's thumb. In addition to holding the endotracheal intubation assistance device onto the practitioner's thumb, the sleeve also serves as a safety barrier which protects the practitioner's hand in the event that the patient bites down on the practitioner's hand, while also protecting the patient from cracking and/or chipping a tooth should the patient bite down upon the sleeve. Accordingly, to aid in flexibility of the endotracheal intubation assistance device, but also to avoid harm to the practitioner and to the patient, in an exemplary embodiment the thumb region comprises one or more of a thick rubber; a soft plastic, such as, for example, neoprene; and the like.

The endotracheal intubation assistance device further comprises a blade member which extends from a distal end of the thumb region. The blade member, which essentially serves as an extension of the practitioner's thumb, is configured to assist in the movement of the patient's tongue away from the practitioner's line of sight, and to assist in the insertion of the blade member anterior and/or posterior to the patient's epiglottis so that the patient's glottis may be viewed more readily by the practitioner.

The blade member may comprise a substantially curved shape or a substantially linear shape, depending upon the patient's specific needs and/or based upon the size of the patient. A substantially curved shaped blade member would be appropriate where exposure of the glottis is accomplished by positioning the blade member anterior to the epiglottis, and a substantially linear shaped blade member would be appropriate where exposure of the glottis is accomplished by positioning the blade member posterior to the epiglottis. Additionally, the blade may be formed in a variety of sizes, wherein the specific sized-blade used during the intubation is preferably determined based upon the specific needs of the patient.

Although the blade member may comprise a wide variety of materials, in an exemplary embodiment, the blade member comprises a heavy plastic; a metal, such as, for example, an iron aluminum alloy; and the like. Furthermore, in an exemplary embodiment the thumb region and the blade member may be integrally formed such that the two members may be bonded together by, for example, impregnating, for example, a metal alloy with the thick rubber and/or soft plastic.

Prior to performing an essentially standard digital intubation technique, the endotracheal intubation assistance device first may be applied such that the thumb region of the device covers the practitioner's thumb and the thumb blade extends over the distal end of the practitioner's thumb, i.e., in a direction oppositely situated from the practitioner's wrist. While the patient is in a generally supine position, the practitioner may then tilt the patient's chin upwards while opening the patient's mouth, and maneuver the blade member such that the blade member moves the patient's tongue upwards towards the patient's upper palate, thereby moving the tongue out of the practitioner's line of sight so that the blade member further exposes the patient's glottis. To accomplish such an end, in an exemplary embodiment, the blade member may comprise a length (as measured from a proximal end to a distal end thereof) of about 1.5 inches to about 3 inches, wherein about 2 inches is especially preferred, and a width (as measured from a lateral end to an oppositely situated lateral end thereof) of up to about 0.5 inch to about 2.5 inches, wherein a width of up to about 2 inches is especially preferred.

While the present invention is susceptible of embodiment in various forms, there is shown in the drawings, and will hereinafter be described, presently preferred embodiments with the understanding that the present disclosure is to be considered an exemplification of the invention and is not intended to limit the invention to the specific embodiments herein illustrated.

Figure 2:
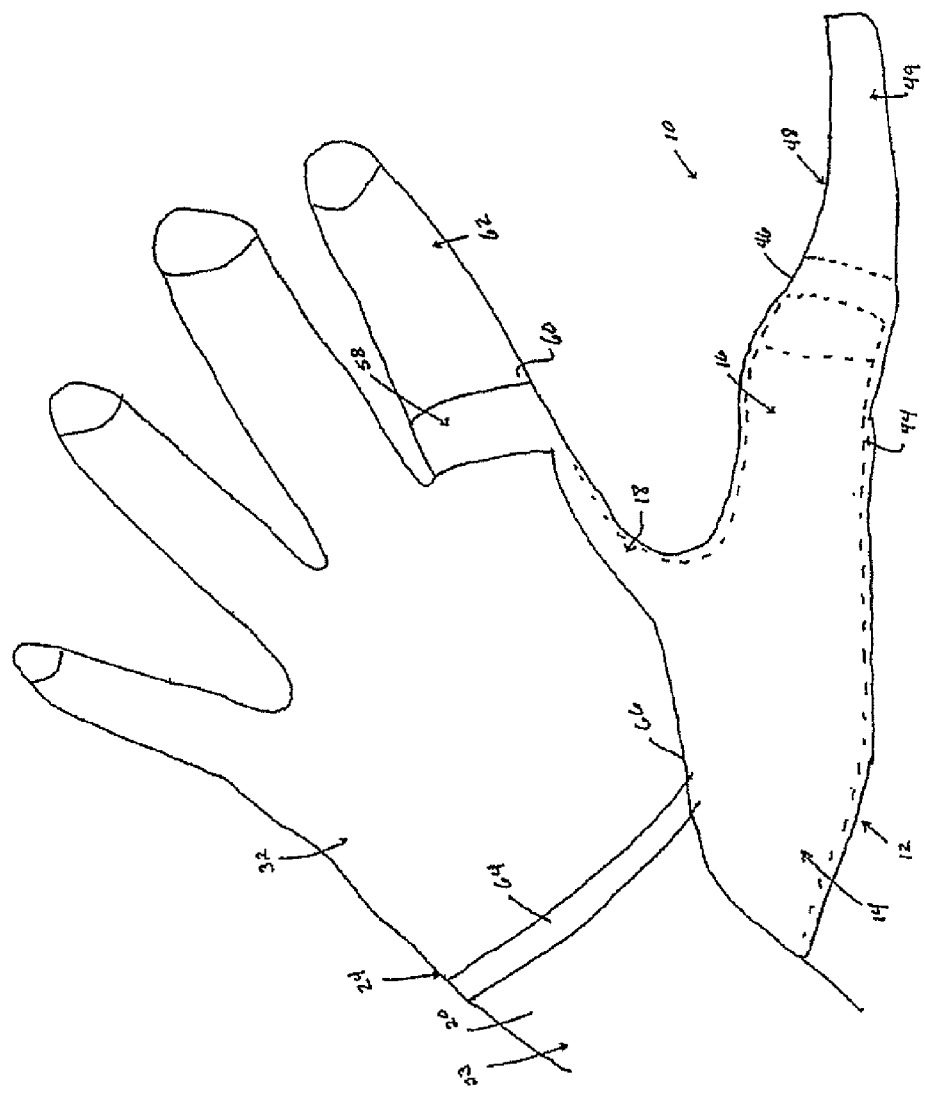
FIG. 2 is a schematic depicting a top side view of an exemplary endotracheal intubation assistance device as applied to a practitioner.
Figure 3:
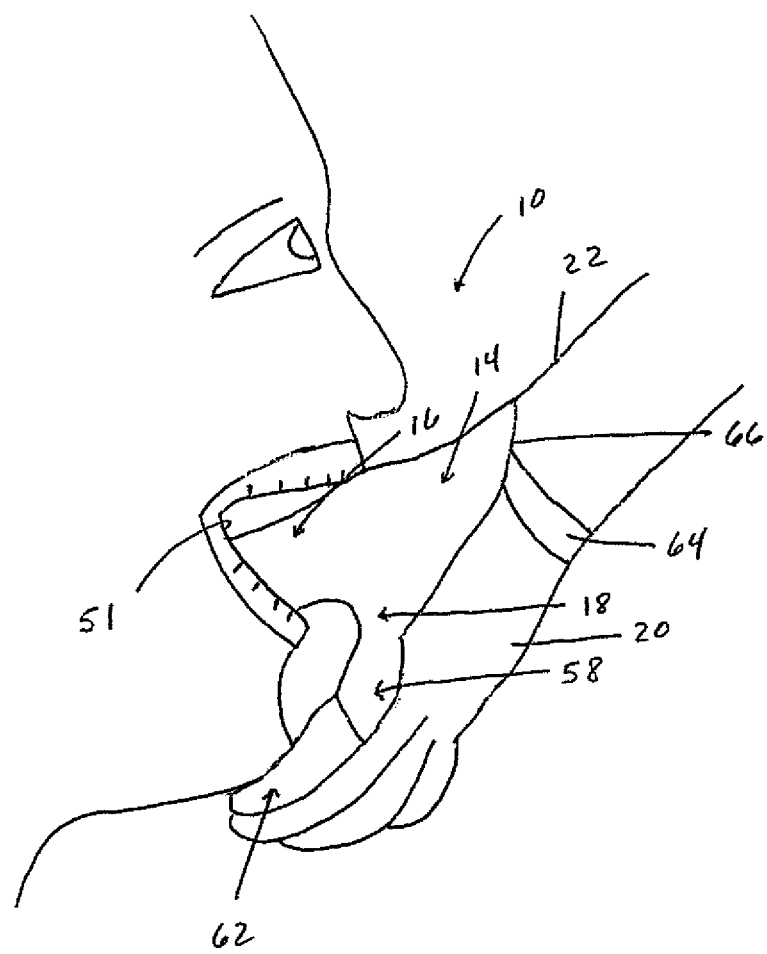
FIG. 3 is a schematic depicting an exemplary application of the endotracheal intubation assistance device depicted in FIG. 2.

Referring to FIGS. 1-3, an exemplary endotracheal intubation assistance device 10 comprises a sleeve 12 having a cuff region 14 coextensive with a thumb region 16 and with a thumb/index finger web region 18. Sleeve 12 preferably comprises a material which provides a protective barrier to the practitioner in the event that the patient bites down on the practitioner's hand during the endotracheal intubation, and which further prevents chipping and/or cracking of the patient's teeth which may otherwise result from such a bite. Cuff region 14 may be configured to overlie at least a portion of a dorsal side 20 and a ventral side 22 of a practitioner's forearm 23, wrist 24, and hand 32, and preferably extends, when properly worn, from a distal region 25 of a radius bone 26 to a distal end 28 of a metacarpal bone I 30.

Thumb/index finger web region 18 continuously extends from cuff region 14 and, when properly worn by a practitioner, may, at least partially, overlie dorsal side 20 and ventral side 22 in the region of the practitioner's metacarpal bone II 38 of an index finger 62.

Thumb region 16 is configured to at least partially envelop a practitioner's thumb 44 in the area of a proximal phlange 40 and of a distal phlange 42 of the practitioner's thumb 44. Extending from a distal end 46 of thumb region 16 is a blade member 48. Although blade member 48 is depicted as having a generally arched-shaped body 49, body 49 may also be substantially linear.

Endotracheal intubation assistance device 10 further comprises a ring member 58 which is physically attached to thumb/index finger web region 18. Ring member 58 is configured to cover, at least partially, a proximal end 60 of index finger 62 of the practitioner's hand 32 in an area approximating the general location of a proximal phlange 63 of index finger 62.

Endotracheal intubation assistance device 10 also comprises a secondary attachment member 64 which is physically attached to a proximal lateral side 66 and to an oppositely situated distal lateral side (not shown) of cuff region 14, wherein an exemplary secondary attachment member comprises a strap. When properly worn by a practitioner, secondary attachment member 64 wraps around dorsal side 20 of the practitioner's wrist 24 and rests thereon to further secure device 10 to the practitioner.

An exemplary application of endotracheal intubation assistance device 10 is depicted in FIG. 3. Referring to FIG. 3, a practitioner dons device 10 by inserting the practitioner's thumb through sleeve 12 such that: cuff region 14 overlies at least a portion of metacarpal bone I 30 of the practitioner's thumb 44, thumb region 16 overlies at least a portion of distal phlange 42 and proximal phlange 40 of the practitioner's thumb 44, and blade member 48 extends away from distal phlange 42 of the practitioner's thumb 44. Additionally, index finger 62 may be inserted through ring member 58 and/or secondary attachment member 64 may be positioned over dorsal side 20 of the practitioner's hand 32 to further secure endotracheal intubation assistance device 10 in place. When performing the intubation, the practitioner may insert the practitioner's thumb 44 into a mouth 51 of the patient. Blade member 48 may be used to move the patient's tongue (not shown) up and away from the practitioner's line of site, and to make apparent the position of the patient's glottis.

Figure 4:
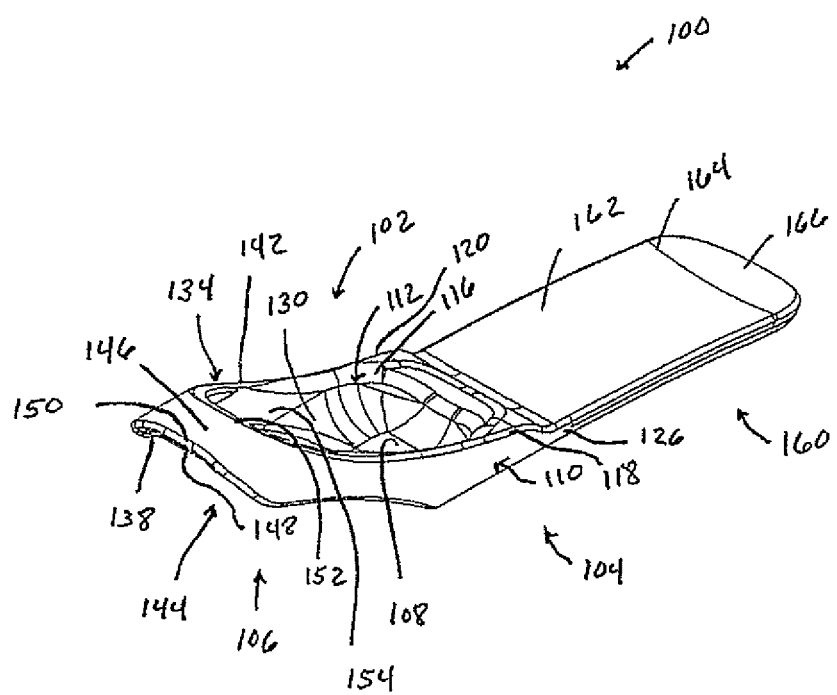
FIG. 4 is a schematic depicting a top perspective view of another exemplary endotracheal intubation assistance device.
Figure 5:
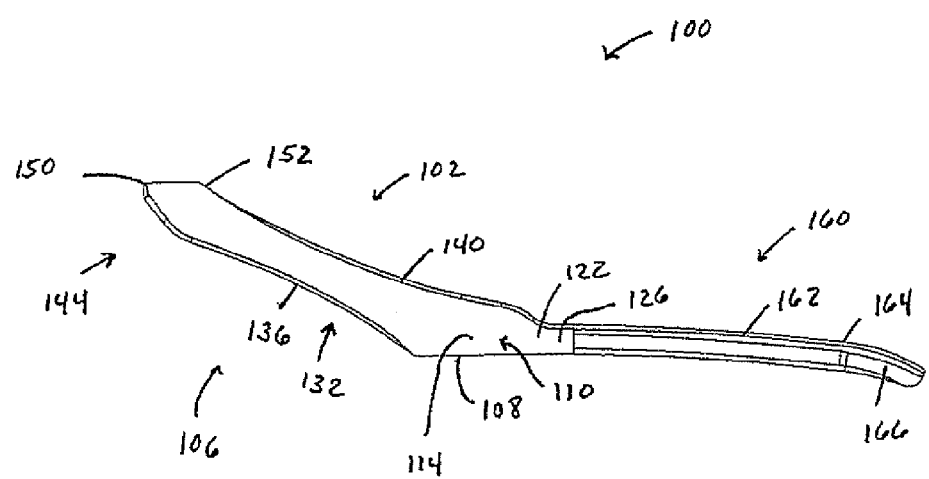
FIG. 5 is a schematic depicting a side view of the endotracheal intubation assistance device depicted in FIG. 4.

Another exemplary endotracheal intubation assistance device is depicted in FIGS. 4 and 5. Here, an endotracheal intubation assistance device 100 comprises a sleeve 102 and a blade member 160. Sleeve 102 is configured to receive a practitioner's thumb and to secure the thumb therein, while blade member 160 is configured to move a patient's tongue and to expose the patient's glottis.

To these ends, sleeve 102 comprises a thumb region 104 and a cuff region 106. Thumb region 104 comprises a bottom wall 108 attached to a proximal lateral wall 110 on an edge thereof and to a distal lateral wall 112 on an oppositely situated edge thereof. Bottom wall 108 is substantially planar.

Each of proximal and distal lateral walls 110 and 112 respectively comprises a body 114 and 116 which terminates at a respective top edge 118 and 120. Each of top edges 118 and 120 first slopes downwardly towards blade member 160, then slopes at an even greater degree downwardly towards blade member 160 to form, along with bodies 114 and 116 and bottom wall 108, an abutment region 122. Each of top edges 118 and 120 then levels off to form, along with bodies 114 and 116 and bottom wall 108, a forward leading member 126. An opening 130 is formed between bottom wall 108, proximal lateral wall 110, and distal lateral wall 112.

Cuff region 106 comprises a proximal side wall 132 oppositely situated from a distal side wall 134, wherein each of proximal and distal side walls 132 and 134 respectively comprises a bottom edge 136 and 138 oppositely situated from a top edge 140 and 142. Each of bottom edges 136 and 138 is contiguous with bottom wall 108 and extends upwardly therefrom to form a generally convex-shaped configuration. Each of top edges 140 and 142 is contiguous with respective top edges 118 and 120 and extends upwardly therefrom to form a generally concave-shaped configuration.

Cuff region 106 further comprises a collar 144. Collar 144 comprises a top side 146 oppositely situated from a bottom side 148 and an anterior edge 150 oppositely situated from a posterior edge 152. Anterior edge 150 is contiguously formed with bottom edges 136 and 138, while posterior edge 152 is contiguously formed with top edges 140 and 142. Top side 146 comprises a generally convex configuration, while bottom side 148 comprises a generally concave configuration. Collar 144, proximal side wall 132 and distal side wall 134 surround an opening 154, wherein opening 154 is contiguously formed with opening 130 of thumb region 104.

Although sleeve 102 may be formed of a wide variety of materials, it is preferred that it is formed of a material that will protect the practitioner in the event that the patient bites down upon the practitioner, while soft enough that the patient's teeth will not crack and/or chip upon impact with the sleeve. Additionally, in an especially preferred embodiment, an exemplary material will confer pliability and elasticity to the sleeve such that the sleeve will adhere securely to the practitioner via a frictional fit.

Blade member 160 comprises a body 162 which is contiguous with forward leading member 126 and extends generally horizontally therefrom and which terminates at an end 164. Blade member 160 further comprises a tip 166 which is contiguous with end 164 and which slopes downwardly therefrom. It is noted that blade tip 166 may be optional when, for example, it is desired to have a strictly generally linear shaped body.

In application, endotracheal intubation assistance device 100 may be worn by a practitioner by inserting the practitioner's thumb through openings 154 and 130 such that a tip of the practitioner's thumb 44 rests directly adjacent to abutment region 122, such that thumb region 104 extends over at least a portion of distal phlange 42 and proximal phlange 40 of the practitioner's thumb 44, and such that cuff region 106 extends over at least a portion of metacarpal bone I of the practitioner's thumb 44.

Although endotracheal intubation assistance device 100 is not shown as having a web region a ring member, and a secondary attachment member as was shown in reference to endotracheal intubation assistance device 10, endotracheal intubation assistance device 100 may be modified to include any one or more of these components such that the component(s) function in a manner substantially similar to that previously disclosed when worn in a similar manner as discussed above with reference to FIGS. 2 and 3.

Although not depicted in the figures, any of the endotracheal intubation assistance devices disclosed herein and/or variations thereto, may include a padding disposed on one or more of the sleeve and the blade member, wherein the padding is configured and formed to protect the practitioner in the event that the patient should bite down upon the practitioner's thumb while the practitioner is performing the endotracheal intubation. Additionally, the padding is preferably configured and formed to prevent injury to the patient's teeth which may result from the patient's biting down upon the endotracheal intubation assistance device. In an exemplary embodiment, the padding is in the form of a sheath that envelops the sleeve and/or the blade member.

It is further contemplated herein that any of the endotracheal intubation assistance devices disclosed herein and/or contemplated herein, may be jointed and aligned with the practitioner's thumb joints to ease movement of the devices. In such an embodiment, the endotracheal intubation assistance device may comprise a sleeve and a blade member substantially similar to what has been previously described herein. Additionally, at a portion of the sleeve which corresponds to the junction between distal phlange 42 and proximal phlange 40 of a practitioner's thumb 44, and at a portion of the sleeve which corresponds to the junction between proximal phlange 40 and metacarpal bone I 30 of the practitioner's thumb 44, the sleeve may be hinged such that it is movable in an upward and downward direction, i.e., towards and away from dorsal side and ventral side 22 of the practitioner's hand 32.

It is noted that for any of the endotracheal intubation assistance devices disclosed herein and/or variants thereof, the practitioner may further wear, in a conventional fashion, a glove, such as a conventionally known latex or neoprene-based medical glove, such that a thumb stall of the glove fits over the sleeve of the endotracheal intubation assistance device and the blade member extends from the thumb stall of the glove, to thereby protect the practitioner from the patient's bodily fluids and to assist in securing the device to the practitioner's thumb. Here, a hole may be formed at the tip of the thumb stall of the glove to thereby allow the blade member to readily extend from the glove. An exemplary embodiment of the integration of endotracheal intubation assistance device 100 with an exemplary glove is depicted in FIG. 6 herein.

Figure 6:
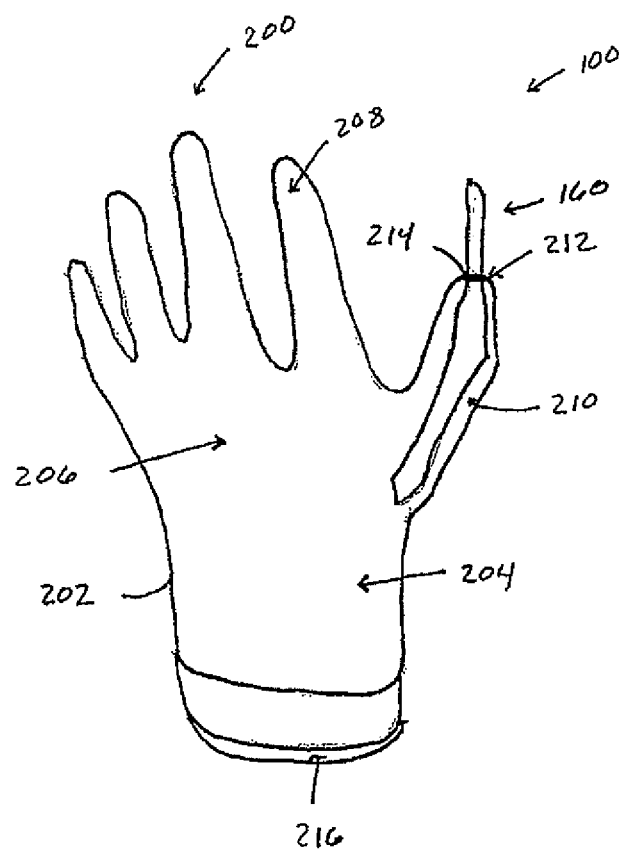
FIG. 6 is a schematic depicting an exemplary application of the endotracheal intubation assistance device depicted in FIGS. 4 and 5 disposed within an exemplary glove.

Referring to FIG. 6, endotracheal intubation assistance device 100 is integrated with a glove 200, wherein glove 200 is depicted as being compatible with a practitioner's left hand, although it is to be understood that the device may be integrated with a right-handed glove as well depending upon the preferences of the practitioner. Glove 200 comprises a ventral side 202 oppositely situated from a dorsal side 204, and further comprises a palm stall 206 from which extends a plurality of finger stalls 208 and a thumb stall 210. A distal tip 212 of thumb stall 210 comprises a hole 214 formed there through. Glove 200 further comprises a hollow interior 216 through which the practitioner's hand is inserted to fit within glove 202 in a conventional manner. Endotracheal intubation assistance device 100 is fitted and installed within thumb stall 210 such that bottom wall 108 of thumb region 104 is directed towards ventral side 202 of thumb stall 210 and top edges 118 and 120 of proximal and distal lateral walls 110 and 112 are directed towards dorsal side 204 of thumb stall 210. Additionally, blade member 160 extends from distal tip 212 of thumb stall 210.

Once endotracheal intubation assistance device 100 is properly applied to the practitioner's thumb 44, the practitioner may begin the endotracheal intubation procedure.

Accordingly, once the patient is lying in a generally supine position, the practitioner may open the patient's mouth, and, with endotracheal intubation assistance device 100 in proper position on the practitioner's thumb, manipulate blade member 160 such that tip 166 moves the patient's tongue away from the practitioner's line of sight, and expose the patient's glottis. Once the pathway to the patient's trachea has been cleared and is readily apparent to the practitioner, the endotracheal intubation may then proceed as is conventionally known.

It is further disclosed herein that any of the endotracheal intubation assistance devices disclosed herein and/or variants thereof may be readily used with a lighting element which assists in the further ready visualization of the patient's glottis.

An exemplary lighting element includes, for example, a light-emitting stylet. An exemplary stylet includes, for example, a stylet disclosed in U.S. patent application Ser. No. 12/622,711 ("'711"), the description of which is hereby incorporated by reference in its entirety. Such stylet is described in '711 as for use with an endotracheal tube and includes a lighting element and a malleable rod which are completely enclosed within an elongated flexible sheath. The elongated flexible sheath has a proximal end and a distal end. In one embodiment, the lighting element is positioned at the distal end of the elongated flexible sheath and the malleable rod is positioned from a proximal end of the lighting element to the proximal end of the elongated flexible sheath. In another embodiment, the lighting element may be positioned between two malleable rods.

Alternatively, the endotracheal intubation assistance device may include a lighting element that is integrated with the sleeve and the thumb blade to further aid in the visualization of the glottis. Such a lighting element may include, for example and without limitation, a chemiluminescent member, a light emitting diode, an infrared light, a light bulb, and the like. An exemplary embodiment of an endotracheal intubation assistance device which incorporates a lighting element is depicted in FIG. 7.

Figure 7:
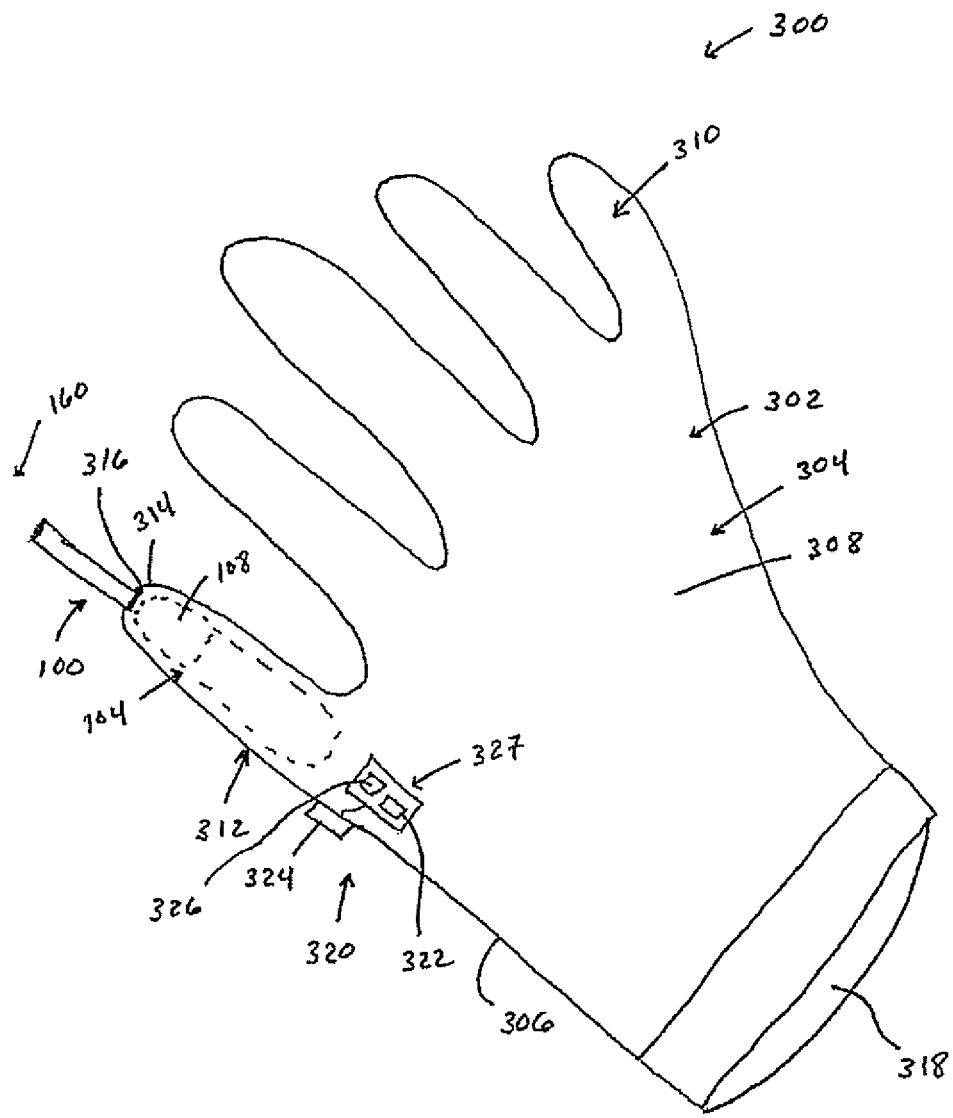
FIG. 7 is a schematic depicting an exemplary apparatus comprising the endotracheal intubation assistance device depicted in FIGS. 4 and 5 in combination with an exemplary light providing sub-assembly.

Referring to FIG. 7, assembly 300 comprises endotracheal intubation assistance device 100 as discussed with reference to FIGS. 4 and 5 herein, incorporated within a glove 302, wherein glove 302 is depicted as being compatible with a practitioner's left hand, although it is to be understood that glove 302 may be compatible with a practitioner's right hand as well. Glove 302 comprises a ventral side 304 oppositely situated from a dorsal side 306, and further comprises a palm stall 308 from which extends a plurality of finger stalls 310 and a thumb stall 312. A distal tip 314 of thumb stall 312 comprises a hole 316 formed there through. Glove 302 further comprises a hollow interior 318 through which the practitioner's hand 32 may be inserted to fit within glove 302. Although glove 302 may be formed of a variety of materials, and may include a conventionally known medical glove, it is preferred that the glove be formed to hold one or more of the components forming the light providing sub-assembly, wherein such sub-assembly is more specifically described below herein. Nevertheless, an exemplary material that may be used to form glove 302 may include silicone.

Endotracheal intubation assistance device 100 is fitted and installed within thumb stall 312 such that bottom wall 108 of thumb region 104 is directed towards ventral side 304 of thumb stall 312 and top edges 118 and 120 of proximal and distal lateral walls 110 and 112 are directed towards dorsal side 306 of thumb stall 312. Additionally, blade member 160 extends from distal tip 314 of thumb stall 312.

Assembly 300 further comprises a light providing sub-assembly 320 disposed on and/or within glove 302. Light providing sub-assembly 320 comprises a light emitting diode 322 and a battery 326 disposed within a housing 327, and a power switch 324, wherein light emitting diode 322, power switch 324, and battery 326 are in electrical communication with one another via conventionally known means. Power switch 324 provides the means whereby the practitioner may activate light emitting diode 322.

Although FIG. 7 depicts a specific placement of light providing sub-assembly 320 in relation to glove 302, it is importantly noted that light providing sub-assembly 320 may be placed anywhere on and/or within glove 302 and/or on and/or within endotracheal intubation assistance device 100, and that the individual components of light providing sub-assembly 320 may be in an arrangement that differs from what is depicted in FIG. 7, wherein the most important consideration in the placement of light providing sub-assembly 320, and of its individual components, lies in the ready accessibility of power switch 324 and in the placement of light emitting diode 322 such that a sufficient amount of light is emitted to further ease in the visibility of the glottis. In use, a practitioner need only actuate light emitting diode 322 via power switch 324.

As evident from the present disclosure, the endotracheal intubation assistance device is lightweight, transportable, inexpensive to manufacture, and easy to use. The endotracheal intubation assistance device further considers and provides for the safety of the practitioner's hand and of the patient's teeth. The endotracheal intubation assistance device also eliminates the "blind" factor encountered when performing a digital intubation as the blade member is configured to remove the tongue from the practitioner's line of sight and to clearly expose the glottis. Additionally, when the endotracheal intubation assistance device is used with a lighting element, such as is disclosed herein, optimum illumination and visualization of the patient's glottis is achieved, thereby increasing the likelihood of the successful patency of the patient's airway.

Accordingly, the endotracheal intubation assistance device provides a viable, lightweight, and easy to use alternative to a laryngoscope, wherein the device has the additional benefit of protecting the practitioner and the patient from resulting from the potential biting down of the patient on the practitioner's hand.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

What is claimed is:

1. An endotracheal intubation assistance device, comprising:
    a sleeve comprising:
        a bottom wall having a proximal-end oppositely situated to a distal end;
        a proximal lateral wall oppositely situated from a distal lateral wall, wherein each of the proximal lateral wall and the distal lateral wall comprises a body which extends horizontally and vertically from the proximal end and the distal end of the bottom wall, wherein the body comprises a top edge oppositely situated from the bottom wall; wherein the top edge slopes downwardly towards the distal end of the bottom wall;

a proximal side wall oppositely situated from a distal side wall, wherein each of the proximal side wall and the distal side wall comprises a bottom edge oppositely situated from a top edge, wherein the bottom edges of the proximal side wall and of the distal side wall are contiguous with the proximal end of the bottom wall, and the top edges of the proximal sidewall and of the distal side wall are contiguous with the top edges of the respective proximal lateral wall and the distal lateral wall; and a collar comprising a top side oppositely situated from a bottom side, and an anterior edge oppositely situated from a posterior edge, wherein the anterior edge is contiguous with the bottom edges of the proximal side wall and the distal side wall, and the posterior edge is contiguous with the top edges of the proximal side wall and the distal side wall; and a blade member which extends from the distal end of the bottom wall; and a glove, wherein the glove comprises a palm stall in association with a thumb stall, wherein the thumb stall has a distal end oppositely situated from the palm stall wherein the distal end of the thumb stall has a hole formed therethrough and further wherein the blade member extends from the hole of the distal end of the thumb stall in a direction opposite to the palm stall.

2. The endotracheal intubation assistance device of claim 1, wherein the top side of the collar comprises a generally convex geometrical configuration, the top edges of the proximal side wall and the distal side wall comprise a generally concave geometrical configuration, and the bottom edges of the proximal side wall and the distal side wall comprise a generally convex geometrical configuration.

3. The endotracheal intubation assistance device of claim 2, further comprising an opening formed between the collar and the bottom wall.

4. The endotracheal intubation assistance device of claim 1, wherein the blade member comprises a generally planar body which terminates at an end directed away from the distal end of the bottom wall, and wherein the blade member further comprises a generally bowed-shaped tip which extends from the end of the body of the blade member.

5. The endotracheal intubation assistance device of claim 1, comprising a light providing sub-assembly in operable communication with one or more of the sleeve, the glove, and the blade member.

6. The endotracheal intubation assistance device of claim 5, wherein the light providing sub-assembly comprises a light source, wherein the light source is selected from the group consisting of a chemiluminescent member, a light emitting diode, an infrared light, and a light bulb.

7. The endotracheal intubation assistance device of claim 6, wherein the light providing sub-assembly comprises a power switch which activates the light source, wherein the power switch is accessible via the glove.

8. A method of assisting a practitioner in performing an endotracheal intubation on a patient, wherein the method comprises:
providing an endotracheal intubation assistance device wherein the endotracheal intubation assistance device comprises:
a sleeve comprising a distal end oppositely situated from a proximal end, wherein the proximal end of the sleeve forms an opening, wherein the sleeve further comprises:
a bottom wall having a proximal-end oppositely situated to a distal end;
a proximal lateral wall oppositely situated from a distal lateral wall, wherein each of the proximal lateral wall and the distal lateral wall comprises a body which extends horizontally and vertically from the proximal end and the distal end of the bottom wall, wherein the body comprises a top edge oppositely situated from the bottom wall; wherein the top edge slopes downwardly towards the distal end of the bottom wall;
a proximal side wall oppositely situated from a distal side wall, wherein each of the proximal side wall and the distal side wall comprises a bottom edge oppositely situated from a top edge, wherein the bottom edges of the proximal side wall and of the distal side wall are contiguous with the proximal end of the bottom wall, and the top edges of the proximal sidewall and of the distal side wall are contiguous with the top edges of the respective proximal lateral wall and the distal lateral wall; and
a collar comprising a top side oppositely situated from a bottom side, and an anterior edge oppositely situated from a posterior edge, wherein the anterior edge is contiguous with the bottom edges of the proximal side wall and the distal side wall, and the posterior edge is contiguous with the top edges of the proximal side wall and the distal side wall; and
a blade member, wherein the blade member comprises a body which extends from the distal end of the sleeve in a direction opposite to the proximal end of the sleeve;
positioning the endotracheal intubation assistance device onto a thumb of the practitioner, wherein the positioning comprises inserting the practitioners thumb within the opening of the sleeve such that the sleeve extends along at least a portion of the practitioner's thumb which comprises a distal phlange, a proximal phlange, and a metacarpal bone;
moving the tongue of the patient with the blade member until the glottis of the patient is visible to the practitioner.

9. The method of claim 8, wherein the endotracheal intubation assistance device further comprises a glove which comprises a thumb stall having a hole formed therethrough, wherein the blade member extends from the hole of the thumb stall, and wherein the positioning of the endotracheal intubation assistance device onto the practitioner's thumb further comprises positioning the practitioner's thumb within the thumb stall of the glove.

10. The method of claim 9, wherein the endotracheal intubation assistance device further comprises a light providing member in operable communication with one or more of the sleeve, the glove, and the blade member, and wherein the method further comprises providing a light source within the mouth of the patient, wherein providing the light source within the patient's mouth comprises actuating the light providing member.

11. The method of claim 10, wherein the tight source is selected from the group consisting of a chemiluminescent member, a light emitting diode, an infrared light, and a light bulb.

* * * * *